United States Patent
Chen et al.

(10) Patent No.: US 9,096,620 B2
(45) Date of Patent: Aug. 4, 2015

(54) MERCAPTOALKYLSILATRANE DERIVATIVE HAVING PROTECTING GROUP AND METHOD OF MANUFACTURING THE SAME

(71) Applicant: National Chung Cheng University, Min-Hsiung Township (TW)

(72) Inventors: Wen-Hao Chen, New Taipei (TW); Lai-Kwan Chau, Chiayi (TW); Chao-Wen Chen, Tainan (TW); Yen-Ta Tseng, New Taipei (TW)

(73) Assignee: National Chung Cheng University, Min-Hsiung Township (TW)

( * ) Notice: Subject to any disclaimer, the term of this patent is extended or adjusted under 35 U.S.C. 154(b) by 0 days.

(21) Appl. No.: 14/195,367

(22) Filed: Mar. 3, 2014

(65) Prior Publication Data

US 2014/0296552 A1    Oct. 2, 2014

(30) Foreign Application Priority Data

Mar. 28, 2013 (TW) .............................. 102111130 A

(51) Int. Cl.
  *C07F 7/02*    (2006.01)
  *C07F 7/18*    (2006.01)
(52) U.S. Cl.
  CPC .................................... *C07F 7/1836* (2013.01)
(58) Field of Classification Search
  CPC ..................................................... C07F 7/1836
  USPC ........................................................ 556/408
  See application file for complete search history.

(56) References Cited

U.S. PATENT DOCUMENTS

| 4,048,206 A | 9/1977 | Voronkov et al. |
| 4,654,368 A * | 3/1987 | Sakamoto et al. ............ 514/493 |
| 2010/0120950 A1 | 5/2010 | Saiki et al. |

FOREIGN PATENT DOCUMENTS

| CN | 1916002 A | 2/2007 |
| CN | 101759891 A | 6/2010 |

OTHER PUBLICATIONS

M. S. Sorokin et al; 1-(trialkylstannylthioalkyl)silatranes; Russian Journal of General Chemistry, Feb. 9, 1998; abstract only.
Office Action of corresponding TW application, published on Oct. 16, 2014.

* cited by examiner

*Primary Examiner* — Porfirio Nazario Gonzalez
*Assistant Examiner* — Kofi Adzamli
(74) *Attorney, Agent, or Firm* — Wang Law Firm, Inc.; Li K. Wang; Stephen Hsu

(57) ABSTRACT

A mercaptoalkylsilatrane derivative having protecting group and a method of manufacturing the same. The mercaptoalkylsilatrane derivative includes: mercaptoalkylsilatrane compound having a mercapto group; a protecting group bonding to sulfur of the mercapto group, wherein the protecting group is used to avoid the chemical reaction of the mercapto group with reactive chemical species, e.g., oxygen, ketone, and aldehyde, etc. Besides, the manufacturing method thereof includes the steps of: providing silane compound having the mercapto group; bonding the protecting group to the mercapto group of the silane compound; performing the chemical reaction of triethanolamine with the silane compound having the protecting group for manufacturing the mercaptoalkylsilatrane derivative having the protecting group.

7 Claims, 5 Drawing Sheets

MERCAPTOALKYLSILATRANE DERIVATIVE HAVING PROTECTING GROUP AND METHOD OF MANUFACTURING THE SAME

CROSS-REFERENCE TO RELATED APPLICATION

This application claims priority to Taiwan Patent Application No. 102111130, filed on Mar. 28, 2013 in Taiwan Intellectual Property Office, the contents of which are hereby incorporated by reference in their entirety.

BACKGROUND OF THE INVENTION

1. Field of the Invention

The present invention is related to a mercaptoalkylsilatrane derivative and method of manufacturing the same, and particularly related to a mercaptoalkylsilatrane derivative having a protecting group and method of manufacturing the same.

2. Description of the Related Art

In recent years, people gradually begin to use biomedical sensors to perform various kinds of detections due to the convenience of biomedical detection technologies. Besides, people tends to perform surface modifications on surface substrates such as metal, plastic, silica, or others to increase sensitivity of detection.

Among surface modification methods, the following two are most common ones. The first one is to use phosphates to perform the surface modification, and the other one is to use silicon compounds to perform the surface modification. For the silicon compound part, people usually use $RSiCl_3$, or $RSi(OR)_3$, compounds to perform surface modification, where R represents an alkyl group and OR represents an alkoxy group. However, these kinds of compounds are rather inconvenient in practical use and the application conditions are severely restricted, thus they are not easy to control and use effectively.

SUMMARY OF THE INVENTION

According to the problem of prior arts, one of the purposes of the present invention is to provide a mercaptoalkylsilatrane derivative having a protecting group and method of manufacturing the same to solve the difficult-to-use problem of the compounds in prior arts.

To achieve the above purpose, a mercaptoalkylsilatrane derivative having the protecting group is provided in the present invention, comprising: a mercaptoalkylsilatrane compound having a mercapto group; and a protecting group, bonded to the sulfur of the mercapto group of the mercaptoalkylsilatrane compound to avoid a chemical reaction of the mercapto group with oxygen or a reactive chemical species having a functional group such as ketone or aldehyde, etc. Furthermore, the chemical formula of the mercaptoalkylsilatrane derivative having the protecting group of the present invention is as shown in Eq. (1) below.

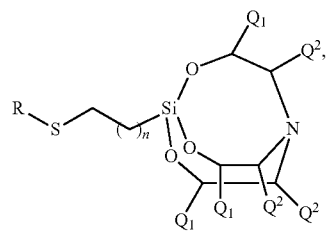

Eq. (1)

, where R is the protecting group; Q1, is hydrogen, an alkyl group, an alkenyl group, an alkynyl group, an aromatic group, halogen, an alcohol group, an ether group, an ester group, or a functional group of alkyl, alkenyl, or alkynyl having silane; Q2, is hydrogen, an alkyl group, an alkenyl group, an alkynyl group, an aromatic group, halogen, an alcohol group, an ether group, an ester group, or a functional group of alkyl, alkenyl, or alkynyl having silane; and n is an integer between 0, and 30.

Furthermore, the protecting group of the mercaptoalkylsilatrane derivative of the present invention can be

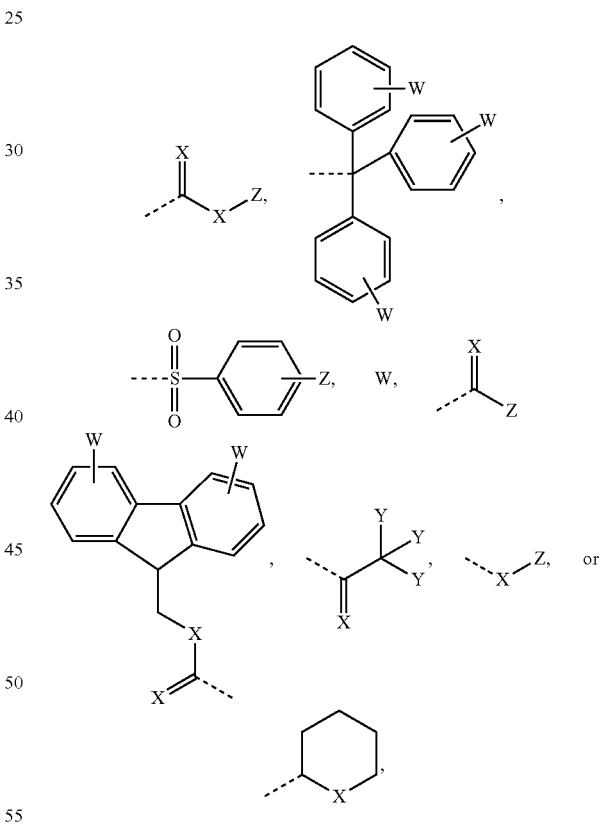

, where X is sulfur (S), oxygen (O), or nitrogen (N); Y is hydrogen (H) or fluorine (F); W is halogen, a hydroxyl group, an alkyl group, an alkenyl group, an alkynyl group, an ester group, or an ether group; Z is an alkyl group, an alkenyl group, an alkynyl group, an allyl group, an ester group, an ether group, a benzyl group, or an aromatic group.

Besides, the protecting group of the mercaptoalkylsilatrane derivative of the present invention may be an acetyl (Ac), a t-butoxycarbonyl (t-Boc), a benzyloxycarbonyl (Cbz), a 9-fluorenylmethoxycarbonyl (Fmoc), a 2-methoxyethoxymethyl (MEM), a methoxymethyl (MOM), a methylthiomethyl (MTM), a phthaloyl (Phth), a p-methoxybenzyl (PMB), a pivaloyl (Piv), a (2-tetrahydropyranyl) (THP), a triphenylmethyl (Tr), a biphenylisopropyloxycarbonnyl (BPoc), a tosyl, a formyl, or a trifluoroacetyl.

Therefore, one of the features of the mercaptoalkylsilatrane derivative of the present invention is by bonding the protecting group to the mercapto group of the mercaptoalkylsilatrane compound to prevent the mercapto group from having a chemical reaction of the mercapto group with oxygen or a reactive chemical species having a functional group such as ketone or aldehyde, etc., such that the mercaptoalkylsilatrane derivative can maintain better stability in air and becomes easier to preserve and use.

Besides, a manufacturing method of the mercaptoalkylsilatrane derivative is further proposed in the present invention, comprising the following steps to manufacture the aforementioned mercaptoalkylsilatrane derivative having the protecting group of the present invention: providing a silane compound having a mercapto group; bonding a protecting group to the mercapto group of the silane compound; and performing a chemical reaction of the silane compound having the protecting group with triethanolamine to manufacture the mercaptoalkylsilatrane derivative having the protecting group of the present invention.

Furthermore, the silane compound can be a silane compound having an alkyl group of 1-30 carbon bonds, preferred to be a silane compound having an alkyl group of 3-11 carbon bonds, and better to be a silane compound have an alkyl group of 3 carbon bonds, and the silane compound having an alkyl group of 3 carbon bonds in this embodiment is a (3-mercaptopropyl)trimethoxysilane.

Besides, the step of bonding the protecting group to the mercapto group of the silane compound is to perform a chemical reaction of the silane compound with an acid anhydride or an acid halide. Furthermore, the acid anhydride and the acid halide include a protecting group.

In addition, the step of performing the chemical reaction of the silane compound with the triethanolamine further includes adding in a dichloromethane ($CH_2Cl_2$) solution to crystallize or precipitate the mercaptoalkylsilatrane derivative of the present invention.

Besides, the step of bonding the protecting group further includes adding potassium carbonate ($K_2CO_3$) and acetonitrile.

In summary, the mercaptoalkylsilatrane derivative having the protecting group and method of manufacturing the same of the present invention may have one or more characteristics and advantages as described below:

(1) By means of bonding the protecting group to the mercapto group of the mercaptoalkylsilatrane compound, the protecting group is able to prevent the mercapto group from having a chemical reaction with oxygen or a reactive chemical species having a functional group such as ketone or aldehyde, etc., such that the mercaptoalkylsilatrane derivative can maintain better stability in air and is easier to preserve and use.

(2) By means of the excellent bonding ability of the mercapto group with most of metals, the mercaptoalkylsilatrane derivative of the present invention can be coated on metals and metal oxides, glass substrates, or plastic substrates.

DETAILED DESCRIPTION OF THE PREFERRED EMBODIMENTS

Figure 1:
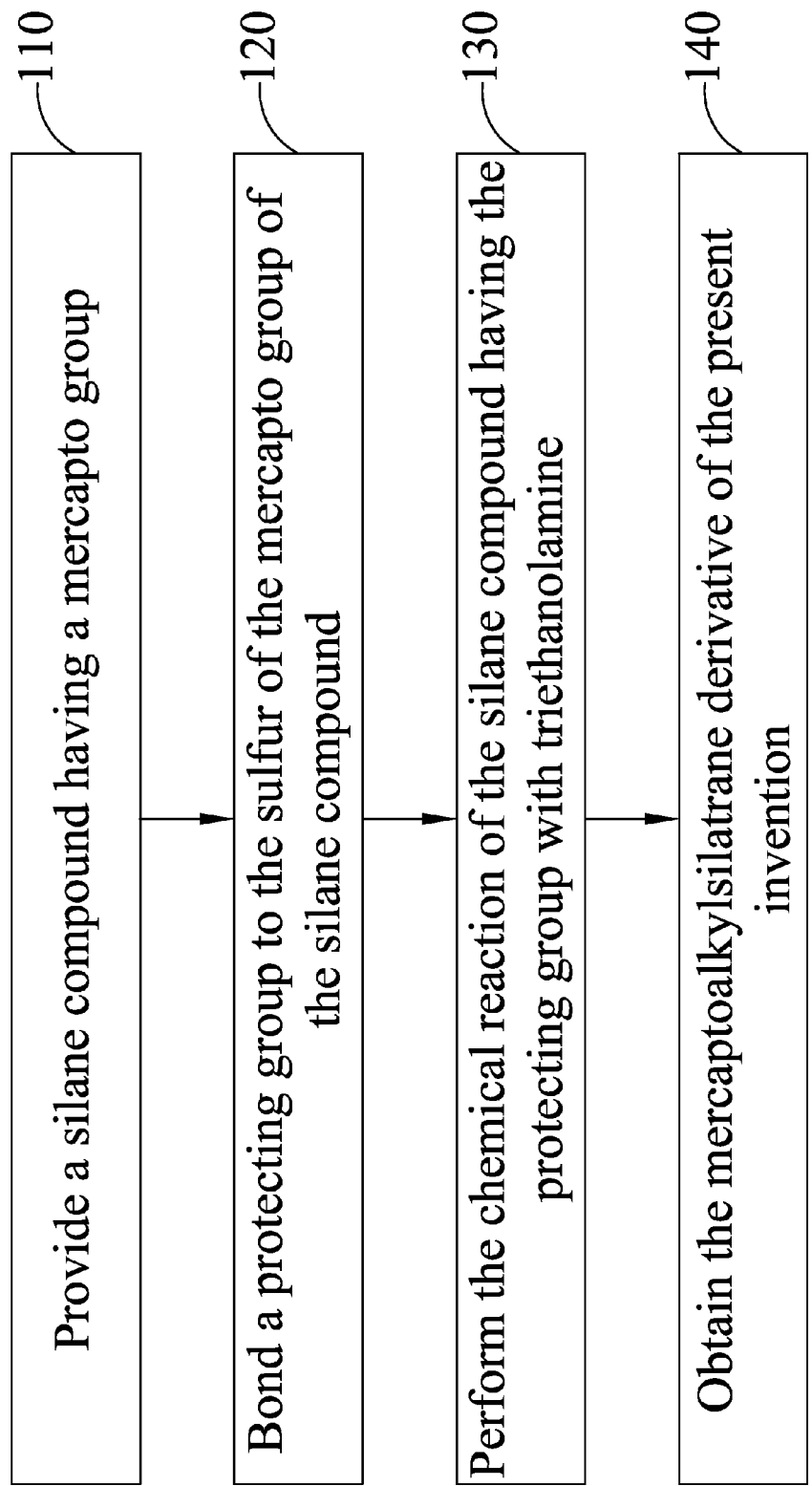
FIG. 1 is a manufacturing flow diagram showing a mercaptoalkylsilatrane derivative having a protecting group according to a preferred embodiment of the present invention.

Referring to FIG. 1, FIG. 1 is a manufacturing flow diagram showing a mercaptoalkylsilatrane derivative having a protecting group according to a preferred embodiment of the present invention. As shown in FIG. 1, the first step of the manufacturing method of a mercaptoalkylsilatrane derivative having a protecting group is to provide a silane compound having a mercapto group, as in Step 110, and the silane compound may be, for example, a silane compound having a mercaptoalkyl group of 1-30 carbon bond, and preferred to be a silane compound having a mercaptoalkyl group of 3-11 carbon bond, and even better to be a silane compound having a mercaptoalkyl group of 3 carbons, i.e., for example, a (3-mercaptopropyl)trimethoxysilane (MPTMS), and the chemical formula of the (n-mercaptoalkyl)trialkoxysilane may be as shown in Eq. (2) below.

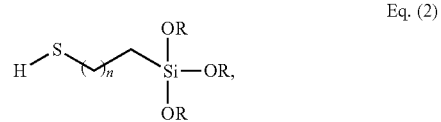

Eq. (2)

where n is an integer within 0 to 30, and OR is an alkoxy group. For example, the alkoxy group may be a methoxy, an ethoxy, a t-butoxy, or other alkoxy groups.

Afterward, a protecting group is bonded to the sulfur of the mercapto group of the mercaptosilane compound, as shown in Step 120, to form a mercaptosilane compound bonding with a protecting group. Furthermore, the chemical formula of the mercaptosilane compound bonded with the protecting group can be, for example, as shown in Eq. (3) below,

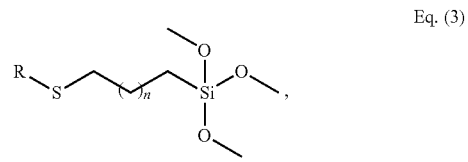

Eq. (3)

where R is the protecting group and n may be an integer within 0 to 30, Moreover, the protecting group may be the ordinary protecting groups, such as alcohol group or nitrogen-containing groups or their derivatives. The protecting group may be, for example,

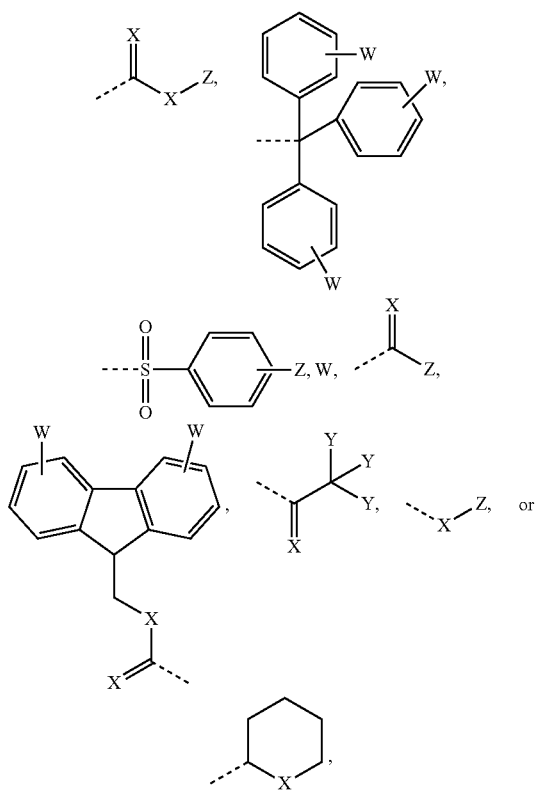

where X is sulfur (S), oxygen (O), or nitrogen (N); Y is hydrogen (H) or fluorine (F); W is halogen, a hydroxyl group, an alkyl group, an alkenyl group, an alkynyl group, an ester group, or an ether group; Z is an alkyl group, an alkenyl group, an alkynyl group, an allyl group, an ester group, an ether group, a benzyl group, or an aromatic group. Therefore, the protecting group of the mercaptoalkylsilatrane derivative of the present invention can be, for example, an acetyl (Ac), a t-butoxycarbonyl (t-Boc), a benzyloxycarbonyl (Cbz), a 9-fluorenylmethoxycarbonyl (Fmoc), a 2-methoxyethoxymethyl (MEM), a methoxymethyl (MOM), a methylthiomethyl (MTM), a phthaloyl (Phth), a p-methoxybenzyl (PMB), a pivaloyl (Piv), a (2-tetrahydropyranyl) (THP), a triphenylmethyl (Tr), a biphenylisopropyloxycarbonnyl (BPoc), a tosyl, a formyl, or a trifluoroacetyl.

For example, the manufacturing method of the mercaptoalkylsilatrane derivative of the present invention may include adding in a compound having a protecting group into the silane compound having a mercapto group, and a chemical reaction is performed between the silane compound having a mercapto group and the protecting group to produce a mercapto silane compound having the protecting group. Furthermore, the chemical formula of the mercaptosilane compound having the protecting group may be, for example, as shown in Eq. (3) above. Besides, the molecule having the protecting group may be, for example, anhydride or acyl chlorides, etc. Therefore, a chemical reaction can be performed between the silane compound and a molecule having a protecting group, such as anhydride and acyl chlorides to form a silane compound having a protecting group. Besides, the manufacturing method of the mercaptoalkylsilatrane derivative of the present invention may further include a step of adding potassium carbonate ($K_2CO_3$) into acetonitrile (ACN) solution having the silane compound to catalyze the chemical reaction of the silane compound having a protected mercapto group.

After Step 120, the chemical reaction between the mercaptosilane compound bonded with the protecting group and triethanolamine is performed in Step 130, in the manufacturing method of the mercaptoalkylsilatrane derivative of the present invention to produce a mercaptoalkylsilatrane derivative having a protecting group. Furthermore, the chemical formula of triethanolamine may be, for example, as shown in Eq. (4) below,

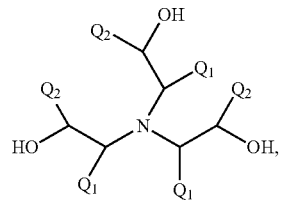

Eq. (4)

and the chemical formula of the mercaptoalkylsilatrane derivative having a protecting group can be as shown in Eq. (1) below,

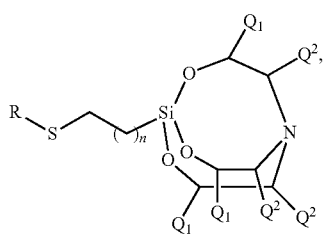

Eq. (1)

where R is the protecting group; Q1, is hydrogen, an alkyl group, an alkenyl group, an alkynyl group, an aromatic group, halogen, an alcohol group, an ether group, an ester group, or a functional group of alkyl, alkenyl, or alkynyl having silane; Q2, is hydrogen, an alkyl group, an alkenyl group, an alkynyl group, an aromatic group, halogen, an alcohol group, an ether group, an ester group, or a functional group of alkenyl, alkenyl, or alkynyl having silane; and n is an integer between 0 and 30.

Besides, the purification steps after finishing the reaction include adding a dichloromethane (DCM) solution to crystallize or precipitate the mercaptoalkylsilatrane derivative having a protecting group, so as to obtain the mercaptoalkylsilatrane derivative of the present invention, as shown in Eq. (1) (such as step 140).

Therefore, the mercaptoalkylsilatrane derivative of the present invention at least includes the mercaptoalkylsilatrane compound having the mercapto group and the protecting group, where the protecting group is bonded to the sulfur of the mercaptoalkylsilatrane compound to prevent the sulfur from having a chemical reaction with oxygen or a reactive chemical species having a functional group such as ketone or aldehyde, to further avoid the mercapto group to be oxidized to become a disulfide bond, and avoid the mercapto group to encounter a high oxidizing compound and be oxidized to become a sulfinyl (S=O) or sulfonyl, such that the mercaptoalkylsilatrane derivative is able to possess better stability in air and easier to preserve and use. Compared with silane compounds, the mercaptoalkylsilatrane derivative of the present invention may provide hydrophobic forces to accelerate the well-ordered self-assembly process, and an aqueous/methanol solution may be utilized to modify a substrate, such as glass, to reduce pollution to environment.

Furthermore, the chemical formula of the mercaptoalkylsilatrane derivative of the present invention is as shown in Eq. (1). In Eq. (1), R is the protecting group; Q1, is hydrogen, an alkyl group, an alkenyl group, an alkynyl group, an aromatic group, halogen, an alcohol group, an ether group, an ester group, or a functional group of alkyl, alkenyl, or alkynyl having silane; Q2, is hydrogen, an alkyl group, an alkenyl group, an alkynyl group, an aromatic group, halogen, an alcohol group, an ether group, an ester group, or a functional group of alkenyl, alkenyl, or alkynyl having silane; and n is an integer between 0 and 30.

Furthermore, the protecting group can be

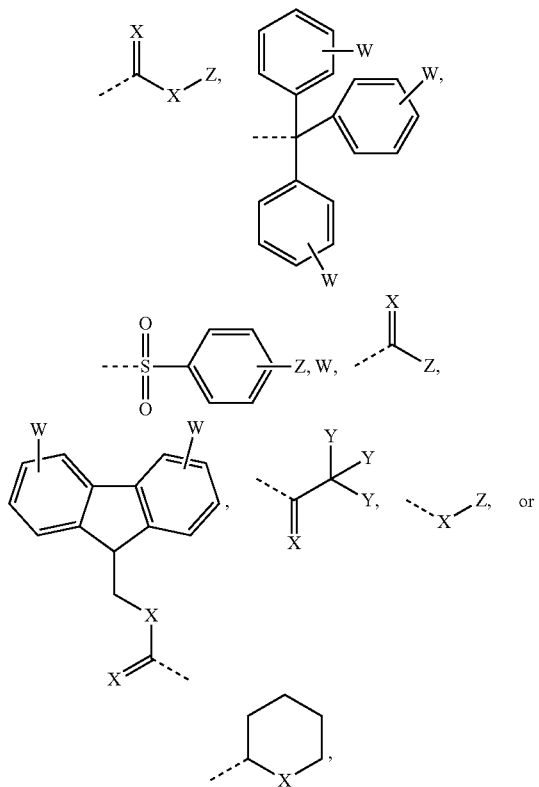

where X is sulfur, oxygen, or nitrogen; Y is hydrogen or fluorine; W is halogen, a hydroxyl group, an alkyl group, an alkenyl group, an alkynyl group, an ester group, or an ether group; Z is an alkyl group, an alkenyl group, an alkynyl group, an allyl group, an ester group, an ether group, a benzyl group, or an aromatic group. For example, the protecting group can be, an acetyl, a t-butoxycarbonyl, a benzyloxycarbonyl, a 9-fluorenylmethoxycarbonyl, a methyl, a methoxymethyl, a methylthiomethyl, a phthaloyl, a p-methoxybenzyl, a pivaloyl, a 2-tetrahydropyranyl, a triphenylmethyl, a biphenylisopropyloxycarbonnyl, a tosyl, a formyl, or a trifluoroacetyl.

For example, the manufacturing method of the mercaptoalkylsilatrane derivative of the present invention begins with providing one equivalent weight of (3-mercaptopropyl) trimethoxysilane (MPTMS) solution, and then a potassium carbonate solution of about 2.5 equivalent weights and about 10 milliliters (ml) of acetonitrile are added in the MPTMS solution. Afterward, about 3 equivalent weights of acetic anhydride is added in, such that a chemical reaction between the acetic anhydride and the MPTMS undergoes in room temperature for 12 hours. After the reaction is completed, the resulting mixture is evaporated to dryness, follows by using dichloromethane (DCM) to re-dissolve the solid, and then a filtering step is performed on the resulting solution.

Afterward, the filtrate is extracted by using a sodium bicarbonate solution of about 10% concentration, and follows by performing the steps of aqueous layer removal, filtering, and evaporation to dryness sequentially to obtain the silane compound having the protecting group, and the protecting group is acetyl. Afterward, a triethanolamine solution of about 2 equivalent weights is added to the silane compound having the protecting group to enable a chemical reaction between the silane compound and the triethanolamine at about 120 degree Celsius for about 3 hours. After the chemical reaction is completed, the resulting mixture is evaporated to dryness and then re-dissolved by using dichloromethane. Finally, pentane is added to precipitate the yellow gel sediment product. The yellow gel sediment is then collected and washed by using pentanoic acid. The yellow gel sediment is the mercaptoalkylsilatrane derivative having a protecting group of the present invention, and the protecting group is acetyl.

To demonstrate that the mercaptoalkylsilatrane derivative having a protecting group of the present invention after modification on a substrate, such as glass, will have a better preservation property, substrates modified with the mercaptoalkylsilatrane derivative after standing in ambient environment at different standing times are allowed to react with gold nanoparticles and the results are compared with substrates modified with other silicon compounds. In this case, the surface plasmon resonance of gold nanoparticle, which has an absorption peak at the wavelength of 530 nanometer, is utilized for subsequent absorbance measurements at that wavelength. Wherein, three kinds of silicon compounds, a mercaptoalkylsilatrane derivative having the protecting group, a mercaptoalkylsilatrane compound having no protecting group, and (3-mercaptopropyl)trimethoxysilane, are modified on glass slides. At zero standing time, the absorbance of the glass slide modified with the silicon compound upon reaction with the gold nanoparticles is set as 100% activity, and the absorbance of the glass slides modified with the three silicon compounds upon reaction with the gold nanoparticles are compared after various standing time periods in air.

Figure 2:
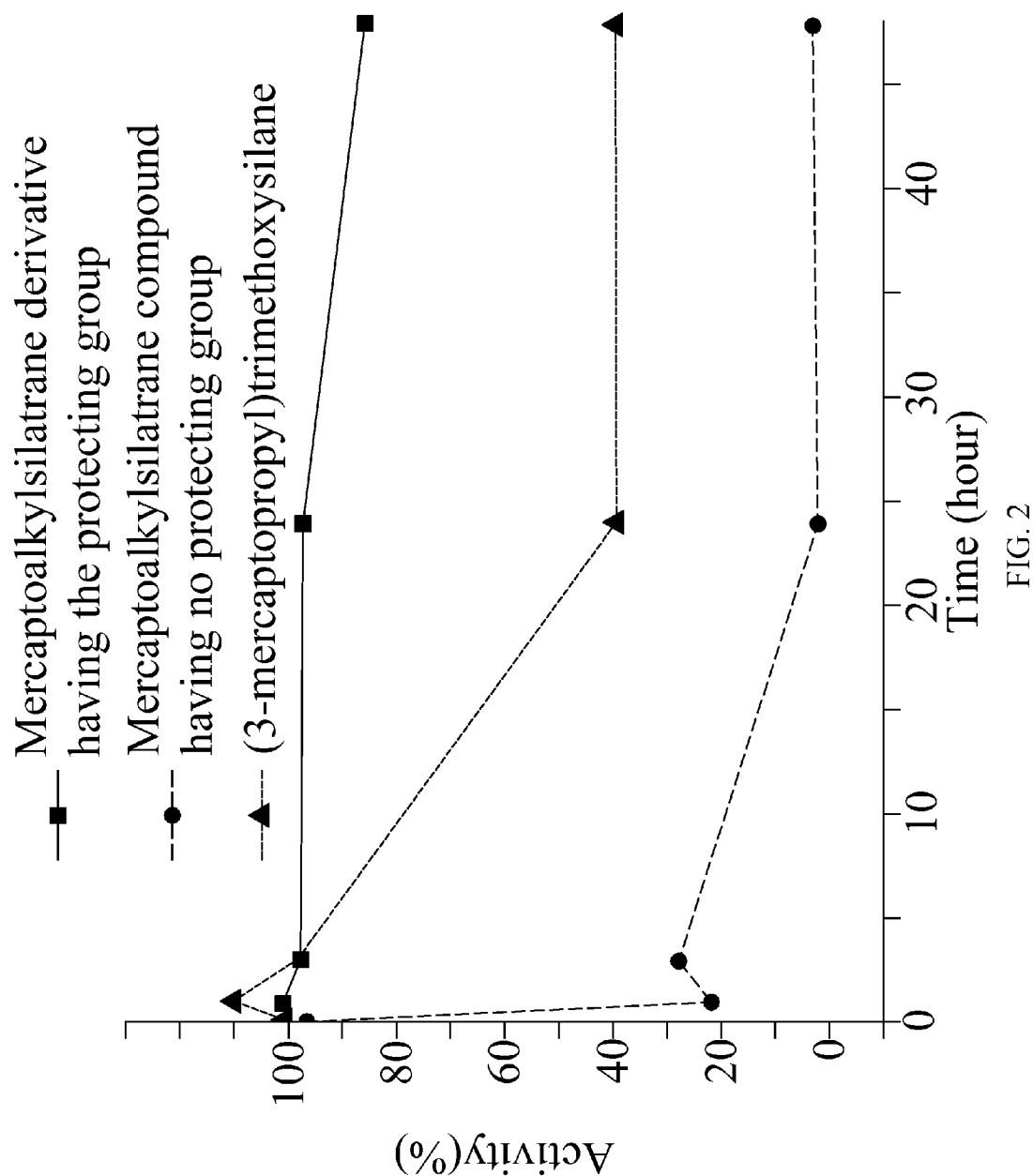
FIG. 2 is an activity versus standing time relationship diagram showing a mercaptoalkylsilatrane derivative having the protecting group according to a first preferred embodiment of the present invention.

Referring to FIG. 2, FIG. 2 is an activity versus standing time relationship diagram showing a mercaptoalkylsilatrane derivative having the protecting group according to a first preferred embodiment of the present invention, where the term "activity" represents the ratio of the absorbance (relative absorbance) at the wavelength of 530 nanometers of the glass slide modified with the silicon compound upon reaction with the gold nanoparticles at a certain standing time to that at zero standing time. Specifically, there are plenty of free electrons moving on the surface of nanometal. When an incident light passes through the nanometal particle, the free electrons interact with the incident electro-magnetic field to absorb the energy of light at a specific frequency so as to cause the phenomenon of coherent electron oscillation, known as particle plasmon resonance (PPR). Take a spherical gold nanoparticle as an example, a gold nanosphere of a 13 nm diameter will absorb a green light of 530 nm wavelength and presents a red color. Through investigating the spectral absorption of the gold nanoparticles on the substrate, the fixing of the gold nanoparticles on the surface of the substrate by self-assembly can be observed and related to the activity of the mercapto group. Furthermore, the mercaptoalkylsilatrane derivative having the protecting group of the present invention can be used as the functional layer for self-assembly of gold nanoparticles.

Furthermore, the horizontal axle of FIG. 2 represents the standing time, while the vertical axis represents the relative absorbance at the wavelength of 530, nanometers of the glass slide modified with the silicon compound upon reaction with the gold nanoparticles at a certain standing time to that at zero standing time. When the mercaptoalkylsilatrane derivative having the protecting group of acetyl of the present invention is modified on the glass slide after standing in air for 48 hours, the modified surface remain 90% activity to react with the gold nanoparticles. When the mercaptoalkylsilatrane compound having no protecting group and (3-mercaptopropyl)trimethoxysilane are modified on the glass slides after standing in air for 24 hours, however, the modified surfaces will have their activities drop below 50% as compared to those with zero standing time, as shown in FIG. 2. Therefore, the mercaptoalkylsilatrane derivative having the protecting group of the present invention has the best stability in air, i.e., the mercaptoalkylsilatrane derivative having the protecting group of the present invention has a better preservation property.

Figure 3:
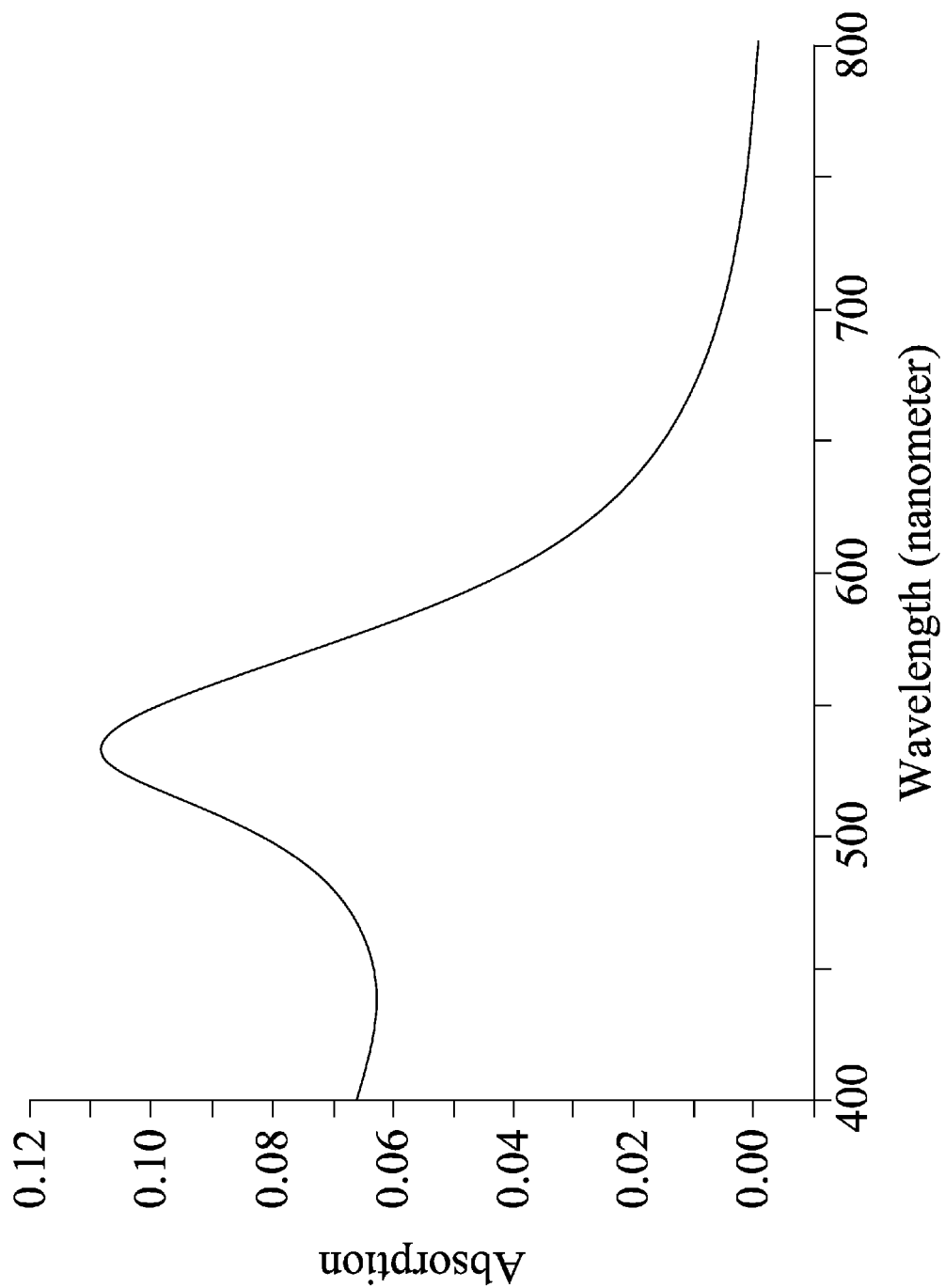
FIG. 3 is an absorption spectrum diagram showing gold nanoparticles bonding to a substrate by using a mercaptoalkylsilatrane derivative having the protecting group according to the first preferred embodiment of the present invention.

Besides, the mercaptoalkylsilatrane derivative having the protecting group of the present invention can be modified on the substrate in shorter time, and maintain the same capability to fix gold nanoparticles on the surface. Referring to FIG. 3, FIG. 3 is an absorption spectrum diagram showing gold nanoparticles bonding to a substrate modified by a mercaptoalkylsilatrane derivative having the protecting group according to the first preferred embodiment of the present invention. As shown in FIG. 3, the gold nanoparticles bonded to the substrate modified with the mercaptoalkylsilatrane derivative having the protecting group of acetyl of the present invention can fix gold nanoparticles on the surface.

Furthermore, the manufacturing method of the mercaptoalkylsilatrane derivative of the present invention in the second preferred embodiment is, for example, to provide the (3-mercaptopropyl)trimethoxysilane solution of about 1, equivalent weight at first, and add in the potassium carbonate solution of about 2.5 equivalent weights and about 10 milliliter (ml) of acetonitrile into the (3-mercaptopropyl)trimethoxysilane solution. Afterward, a solution of about 1.2 equivalent weights of triphenylmethyl chloride is added in, such that a chemical reaction between triphenylmethyl chloride and (3-mercaptopropyl)trimethoxysilane undergoes in room temperature for 12 hours. After the reaction is completed, the resulting mixture is evaporated to dryness, follows by using dichloromethane (DCM) to re-dissolve the solid, and then a filtering step is performed on the resulting solution. Afterward, the filtrate is extracted by using pentane to obtain a mercaptoalkylsilane compound having a protecting group of triphenylmethyl.

Afterward, a triethanolamine solution of 3 equivalent weights is added to the silane compound having the protecting group to enable a chemical reaction between the silane compound and triethanolamine at about 100 degree Celsius for about 6 hours. After the chemical reaction is completed, the resulting mixture is evaporated to dryness and the solid is washed by using pentanoic acid. Finally, a mixture of dichloromethane and pentane in 1:1 proportion is added to precipitate the yellow translucent sediment product. The yellow translucent sediment is the mercaptoalkylsilatrane derivative having a protecting group of the present invention, wherein the protecting group is triphenylmethyl.

Figure 4:
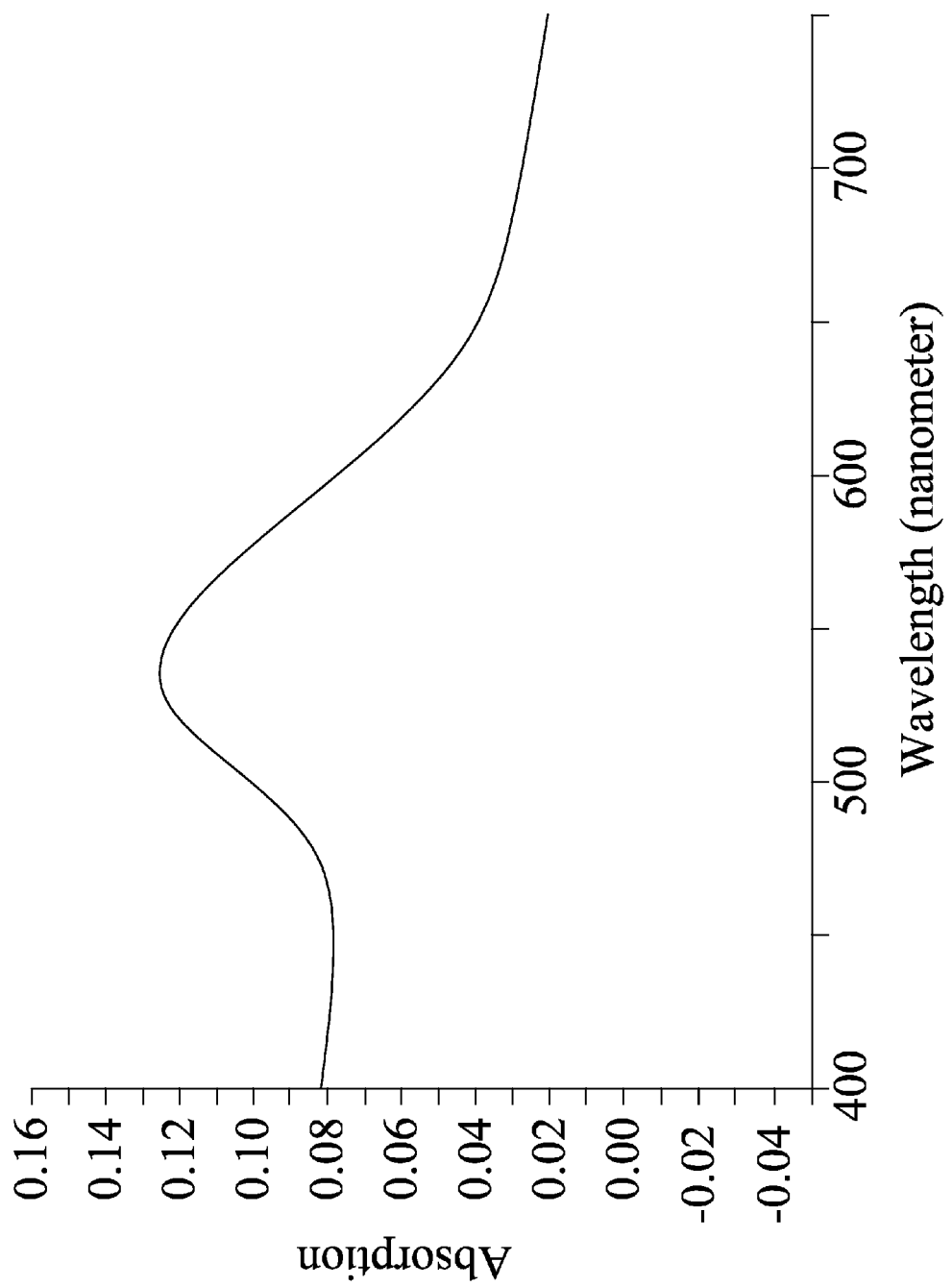
FIG. 4 is the absorption spectrum diagram showing gold nanoparticles bonding to a substrate by using a mercaptoalkylsilatrane derivative having the protecting group according to a second preferred embodiment of the present invention.

Experimental data are obtained to confirm that the mercaptoalkylsilatrane derivative having a protecting group of the present invention can be modified on a substrate, such as glass, and the gold nanoparticles bonded to the substrate modified with the mercaptoalkylsilatrane derivative having a protecting group of the present invention absorb light at the PPR wavelength. Referring to FIG. 4, FIG. 4 is the absorption spectrum diagram showing gold nanoparticles bonded to a substrate modified with a mercaptoalkylsilatrane derivative having the protecting group according to a second preferred embodiment of the present invention. As shown in FIG. 4, the gold nanoparticles bonded to the substrate modified with the mercaptoalkylsilatrane derivative having the protecting group of triphenylmethyl of the present invention absorb light of a peak wavelength of about 530 nanometers.

Furthermore, the manufacturing method of the mercaptoalkylsilatrane derivative of the present invention in the third preferred embodiment is, for example, to provide the (3-mercaptopropyl)trimethoxysilane solution of about 1, equivalent weight at first, and add in the potassium carbonate solution of about 2.5 equivalent weights and about 10 milliliter (ml) of acetonitrile into the (3-mercaptopropyl)trimethoxysilane solution. Afterward, an acid anhydride solution of t-butoxycarbonyl of about 1.2 equivalent weights is added in, such that a chemical reaction between acid anhydride and (3-mercaptopropyl)trimethoxysilane undergoes in room temperature for 12 hours. After the reaction is completed, the resulting mixture is evaporated to dryness, follows by using dichloromethane to re-dissolve the solid, and then a filtering step is performed on the resulting solution. Afterward, the filtrate is extracted by using a sodium carbonate ($Na_2CO_3$) solution to obtain a mercaptoalkylsilane compound having a protecting group of t-butoxycarbonyl.

Afterward, a triethanolamine solution of 1.2 equivalent weights is added to the silane compound having the protecting group to enable a chemical reaction between the silane compound and triethanolamine at about 100 degree Celsius for about 6 hours. After the chemical reaction is completed, the resulting mixture is evaporated to dryness and the solid is washed by using icy pentane. Finally, a mixture of dichloromethane and pentane in 1:1 proportion is added to precipitate the yellow translucent sediment product. The yellow translucent sediment is the mercaptoalkylsilatrane derivative having a protecting group of the present invention, wherein the protecting group is t-butoxycarbonyl.

Figure 5:
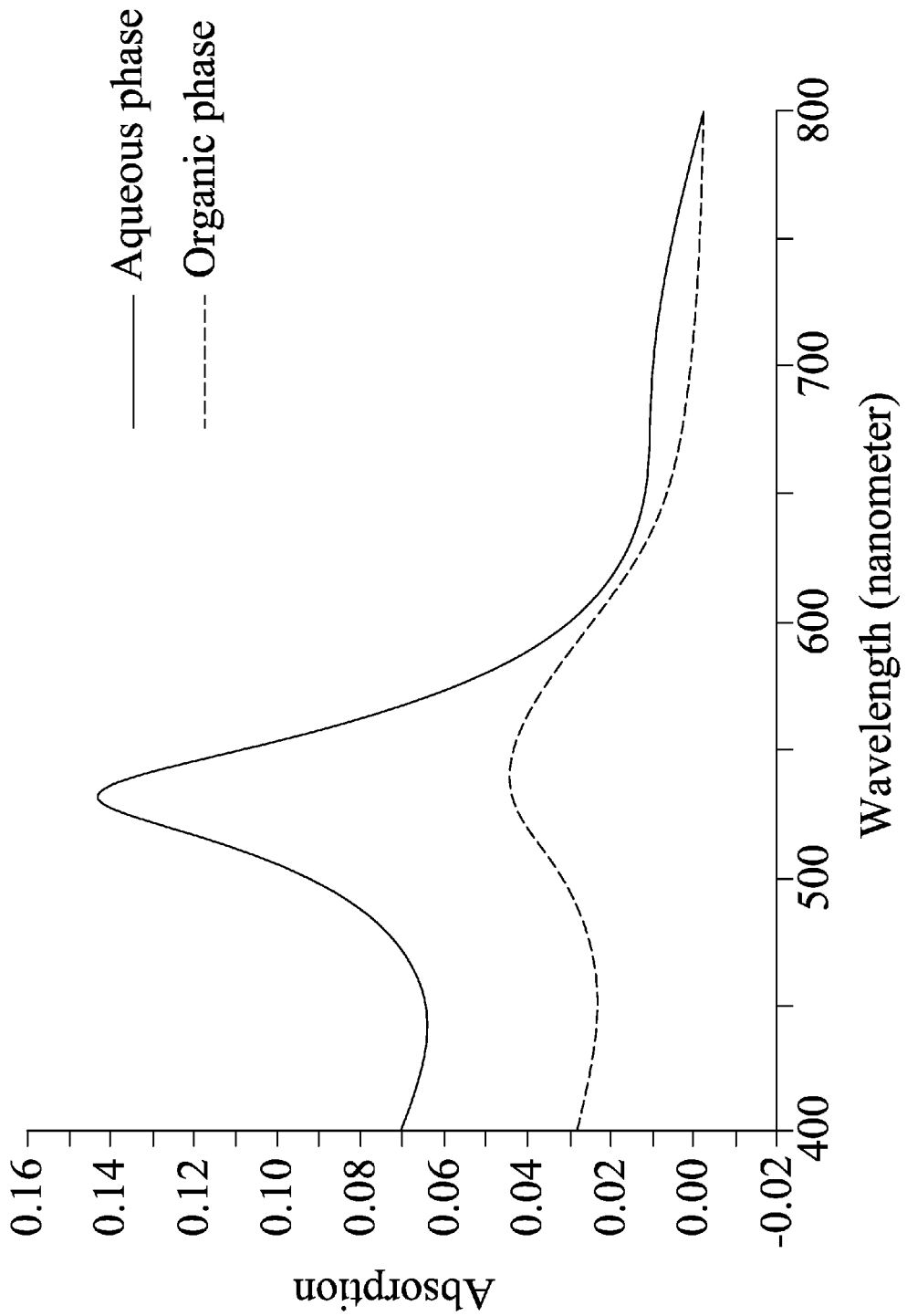
FIG. 5 is an absorption spectrum diagram showing gold nanoparticles bonding to a substrate by using a mercaptoalkylsilatrane derivative having the protecting group according to the third preferred embodiment of the present invention.

Experimental data are obtained to confirm that mercaptoalkylsilatrane derivative having a protecting group of t-butoxycarbonyl of the present invention can be modified on a substrate, such as glass, and the gold nanoparticles bonded to the substrate modified with the mercaptoalkylsilatrane derivative having a protecting group of the present invention absorb light at the PPR wavelength. Referring to FIG. 5, FIG. 5 is an absorption spectrum diagram showing gold nanoparticles bonding to a substrate modified with a mercaptoalkylsilatrane derivative having the protecting group according to the third preferred embodiment of the present invention. As shown in FIG. 5, the gold nanoparticles bonded to the substrate modified with the mercaptoalkylsilatrane derivative having the protecting group of t-butoxycarbonyl of the present invention absorb light at a peak wavelength of about 530 nanometers.

Furthermore, the manufacturing method of the mercaptoalkylsilatrane derivative of the present invention in the fourth preferred embodiment is, for example, to provide the (3-mercaptopropyl)trimethoxysilane solution of about 1 equivalent weight at first, and add in the potassium carbonate solution of about 2.5 equivalent weights and about 10 milliliter (ml) of acetonitrile into the (3-mercaptopropyl)trimethoxysilane solution. Afterward, a solution of 9-fluorenylmethoxycarbonyl chloride of about 2 equivalent weights is added, such that a chemical reaction between fluorenylmethoxycarbonyl chloride and (3-mercaptopropyl)trimethoxysilane undergoes in room temperature for 36 hours. After the reaction is completed, the resulting mixture is evaporated to dryness, follows by using dichloromethane to re-dissolve the solid, and then a filtering step is performed on the resulting solution. Afterward, the filtrate is extracted by using a 10% sodium bicarbonate solution to obtain a silane compound having a protecting group of 9-fluorenylmethoxycarbonyl.

Afterward, a triethanolamine solution of 3 equivalent weights is added to the silane compound having the protecting group to enable a chemical reaction between the silane compound and triethanolamine at about 160 degree Celsius for about 3 hours. After the chemical reaction is completed, the resulting mixture is evaporated to dryness and the solid is re-dissolved by using dichloromethane. Finally, pentane is added to precipitate the yellow gel sediment product. The yellow gel sediment is the mercaptoalkylsilatrane derivative having a protecting group of the present invention, wherein the protecting group is 9-fluorenylmethoxycarbonyl.

In summary, the mercaptoalkylsilatrane derivative of the present invention at least comprises the mercaptoalkylsilatrane compound having the mercapto group, and the protecting group, where the protecting group may be the commonly used protecting group, such as the alcohol group or nitrogen-containing groups or their derivatives. Furthermore, the protecting group is bonded to the sulfur of the mercapto group of the mercaptoalkylsilatrane compound, so as to prevent the mercapto group from having a chemical reaction with oxygen or a reactive chemical species having a functional group such as ketone or aldehyde, etc., such that the mercaptoalkylsilatrane derivative of the present invention can maintain better stability in air and is easier to preserve and use.

The present invention has been described with reference to the foregoing preferred embodiments, it will be understood that the invention is not limited to the details thereof. Various equivalent variations and modifications may still occur to those skilled in this art in view of the teachings of the present invention. Thus, all such variations and equivalent modifications are also embraced within the scope of the invention as defined in the appended claims.

What is claimed is:

1. A manufacturing method of a mercaptoalkylsilatrane derivative, at least comprising the following steps of:
   providing a silane compound having a mercapto group;
   bonding a protecting group to the mercapto group of the silane compound; and
   performing a chemical reaction of the silane compound having the protecting group with triethanolamine to manufacture the mercaptoalkylsilatrane derivative having the protecting group, wherein the chemical formula of the mercaptoalkylsilatrane derivative is

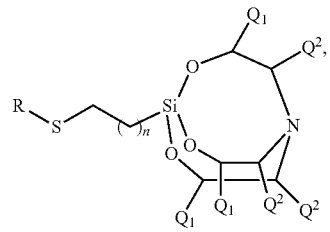

and R is the protecting group, n is an integer between 0 and 30, Q1 is hydrogen, an alkyl group, an alkenyl group, an alkynyl group, an aromatic group, halogen, an alcohol group, an ether group, an ester group, or a functional group of alkyl, alkenyl, or alkynyl having silane, Q2 is hydrogen, an alkyl group, an alkenyl group, an alkynyl group, an aromatic group, halogen, an alcohol group, an ether group, an ester group, or a functional group of alkenyl, alkenyl, or alkynyl having silane.

2. The manufacturing method of the mercaptoalkylsilatrane derivative of claim 1, wherein the protecting group is

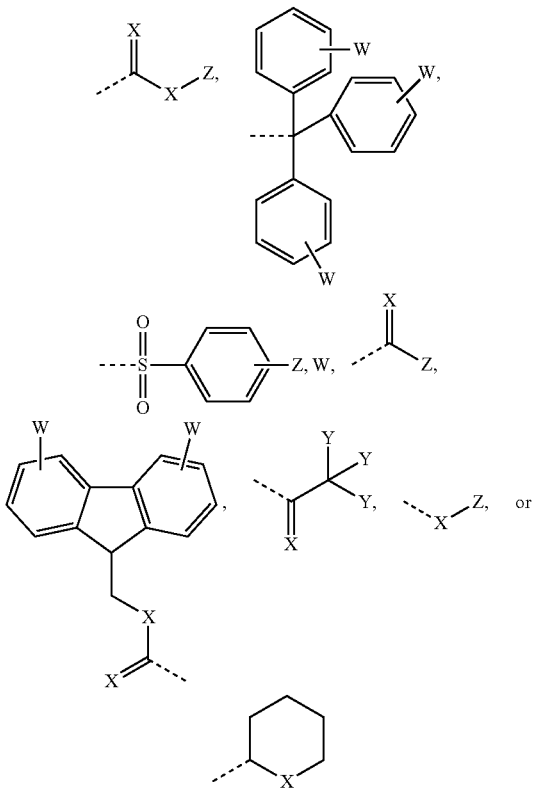

wherein X is sulfur, oxygen, or nitrogen, Y is hydrogen or fluorine, W is halogen, a hydroxyl group, an alkyl group, an alkenyl group, an alkynyl group, an ester group, or an ether group, Z is an alkyl group, an alkenyl group, an alkynyl group, an allyl group, an ester group, an ether group, a benzyl group, or an aromatic group.

3. The manufacturing method of the mercaptoalkylsilatrane derivative of claim 1, wherein the protecting group is an acetyl, a t-butoxycarbonyl, a benzyloxycarbonyl, a 9-9-fluorenylmethoxycarbonyl, a methyl, a methoxymethyl, a methylthiomethyl, a phthaloyl, a p-methoxybenzyl, a pivaloyl, a 2-tetrahydropyranyl, a triphenylmethyl, a biphenylisopropyloxycarbonnyl, a tosyl, a formyl, or a trifluoroacetyl.

4. The manufacturing method of the mercaptoalkylsilatrane derivative of claim 1, wherein the silane compound is (3-mercaptopropyl)trimethoxysilane.

5. The manufacturing method of the mercaptoalkylsilatrane derivative of claim 1, wherein the step of bonding the protecting group to the mercapto group of the silane compound is to perform a chemical reaction of the silane compound with an acid anhydride or an acyl chlorides, wherein the acid anhydride or the acyl chlorides comprise the protecting group.

6. The manufacturing method of the mercaptoalkylsilatrane derivative of claim 1, wherein the step of performing the chemical reaction of the silane compound having the protecting group with triethanolamine further comprises adding dichloromethane to crystallize or precipitate the mercaptoalkylsilatrane derivative.

7. The manufacturing method of the mercaptoalkylsilatrane derivative of claim 1, wherein the step of bonding the protecting group further comprises adding potassium carbonate and acetonitrile.

* * * * *